United States Patent [19]
Rubin

[11] Patent Number: 5,707,336
[45] Date of Patent: Jan. 13, 1998

[54] VENTRICULAR ASSIST DEVICE

[75] Inventor: Leo Rubin, Suffern, N.Y.

[73] Assignee: Cardassist Incorporated, Suffern, N.Y.

[21] Appl. No.: 652,522

[22] PCT Filed: Jan. 9, 1995

[86] PCT No.: PCT/US95/00184

§ 371 Date: Jun. 4, 1996

§ 102(e) Date: Jun. 4, 1996

[87] PCT Pub. No.: WO95/18593

PCT Pub. Date: Jul. 13, 1995

[51] Int. Cl.$^6$ ............... A61B 17/00; A61H 7/00
[52] U.S. Cl. ............... 600/17; 606/191; 623/3
[58] Field of Search ............... 600/16, 17; 623/3; 606/191, 201, 202

[56]  References Cited

U.S. PATENT DOCUMENTS

| | | | |
|---|---|---|---|
| 3,730,186 | 5/1973 | Edmunds, Jr. et al. | 606/202 |
| 4,192,293 | 3/1980 | Asrican | 600/17 |
| 5,098,369 | 3/1992 | Heilman et al. | 600/17 |

*Primary Examiner*—William Lewis
*Attorney, Agent, or Firm*—Brumbaugh, Graves, Donohue & Raymond

[57]  ABSTRACT

Cardiac ventricular assist apparatus adapted to be placed by insertion through an incision in the wall of the upper abdomen below the rib cage and an incision in the inferior aspect of the pericardium proximate the heart apex comprises a distensible flexible bladder adapted to be passed through the incision in the pericardium to a position between the pericardial sac and the epicardium. The bladder is of a size such and shape such as to be engageable with a substantial portion of the outer surface of the left ventricle of a heart and is attached to a tube through which a gas can be introduced into it to compress the left ventricle and withdrawn from it to allow the ventricle to fill. A non-dietensible tube joined to the distal edge of the bladder is connected to a source of a fluid by which it can be inflated after insertion of the bladder to deploy the distal edge of the bladder from a collapsed condition in which it is emplaced within the pericardium to an extended condition partly encircling the heart.

16 Claims, 5 Drawing Sheets

VENTRICULAR ASSIST DEVICE

BACKGROUND OF THE INVENTION

Several forms of heart failure can be treated by ventricular assistance, such as by closed chest compression (an aspect of cardio-pulmonary resuscitation), manual heart massage, or mechanical ventricular assistance. Closed chest compression, coupled with medication, must be stopped and replaced by some other treatment if effective rhythm and adequate blood flow are not restored expeditiously. Similarly, while manual heart message can be performed for an indefinite period, it is impractical to do so. Manual message also requires a thoracotomy, with its own morbidity, high cost, and potential complications.

Direct mechanical ventricular assistance has been the subject of considerable research for many years. The requirements for highly specialized equipment and major surgery for implantation has limited widespread applicability, especially in emergency situations.

Maintenance of blood circulation by a failing heart can also be provided by removing blood from the ventricles and pumping it back to the aorta. Indirect mechanical ventricular assistance, like direct assistance, requires extensive surgery. It also involves direct contact between the blood and the apparatus. Blood can clot in areas of the apparatus where flow rates are low, and clots can break away and cause a stroke.

Direct mechanical ventricular assist devices have been described in the medical literature and in patents, the following being exemplary:

U.S. Pat. No. 2,826,193 (Vineberg, 1958)
U.S. Pat. No. 3,034,501 (Hewson, 1962)
U.S. Pat. No. 3,233,607 (Bolie, 1966)
U.S. Pat. No. 3,371,662 (Heid et al., 1968)
U.S. Pat. No. 3,455,298 (Anstadt, 1969)
U.S. Pat. No. 4,048,990 (Goetz, 1977)
U.S. Pat. No. 4,690,134 (Snyders, 1987)
U.S. Pat. No. 5,169,381 (Snyders, 1992)

"First Successful Bridge to Cardiac Transplantation Using Direct Mechanical Ventricular Actuation," J. E. Lowe et al., Ann Thorac Surg 1991; 52:1237–45

"Direct Mechanical Ventricular Actuation: A Review," M. P. Anstadt et al., Resuscitation, 1991; 21:7–23

All of the devices proposed heretofore for direct mechanical ventricular actuation are implaced by performing a thoracotomy, opening the pericardium, and placing a cup-like squeezing element over the ventricles. The squeezing element typically has a rigid or semi-rigid outer cup and two chambers, one for each ventricle, formed by panels of an extensible material attached and sealed to the outer cup. The chambers are periodically inflated with a gas under pressure supplied through a tube leading from a mechanical pump to squeeze the ventricles and discharge blood (systole) and then deflated by evacuation by the mechanical pump to draw blood from the atria (diastole).

The squeezing action of the chambers requires that the outer non-extensible cup-like wall member of the squeezing device sustain the reaction loads of the pressure applied to the heart. That means, in turn, that the element must be sized and shaped to fit the heart snugly. Inasmuch as the exact size of the patient's heart is often not known in advance, it is necessary to have a range of sizes of squeezing elements on hand for selection and use after access to the heart has been obtained. While the need to maintain an inventory of squeezing elements and for measuring the heart and selecting an element of the right size is by no means an insurmountable impediment to clinical use of such devices, it is an inconvenience and delays the operative procedure. In an emergency situation, such as heart arrest during surgery, time is critical. The sooner that normal or near normal blood flow can be restored, the lower is the probability of irreversible damage to the patient due to temporary loss of cardiac function.

Because the ventricular portion of the heart is roughly conical, the squeezing action of the squeezing element against the ventricles tends to push the element away from the heart. Thus, it is necessary to hold the element in place. Anstadt et al. (referred to above) provide retention of the element by applying a vacuum within the squeezing element. Snyders (also referred to above) provides retention by suturing the squeezing element to the pericardium.

In addition to the requirement for highly invasive surgery for implanting the device and the need for closing the pericardium window and the thoracotomy wound if the device is to be left in place for a significant period of time, which will almost always be the case, reoperation is required to remove it. Both the operation to implant the assist device and the operation, if required, to remove it place the patient at additional risk beyond the heart condition that called for its use. Even if thoracotomy is not required for removal of the device, as proposed by Goetz (referred to above), surgical implantation of previously known mechanical ventricular assist devices requires relatively complicated surgery that offers little chance for success unless performed by a skilled surgical team in an operating room.

SUMMARY OF THE INVENTION

One objective of the present invention is to provide ventricular assist apparatus that includes a flexible, inflatable bladder that can be placed in contact with the heart with minimally invasive surgery that can be carried out quickly. It is also an objective to provide ventricular assist apparatus that can be surgically placed in settings other than a hospital operating room, such as in a hospital emergency room or an emergency coronary care vehicle. Still another object is to provide a method of providing ventricular assistance to a failing heart, which can be used for a short period of time to support blood circulation following a cardiac arrest or a longer period of time to maintain heart function while a damaged heart heals or until a replacement heart for transplantation becomes available.

The foregoing objects are attained, in accordance with one aspect of the present invention, by a cardiac ventricular assist apparatus adapted to be placed by insertion through an incision in the wall of the upper abdomen below the rib cage and an incision in the inferior aspect of the pericardium. The apparatus includes a flexible, inflatable bladder that when collapsed can be passed through the incision in the pericardium and guided to a position between the pericardium and epicardium. The inflatable bladder is of a size and shape such as to engage a substantial portion of the outer surface of at least the left ventricle of the heart and is attached to a tube through which a gas can be introduced into it and withdrawn from it. The bladder has a distal edge that is adapted to be located proximate to the atrio-ventricular groove of the heart.

In preferred embodiments, a non-distensible tube is attached to the distal edge of the bladder and is arranged to be connected to a source of a fluid. When fluid is supplied to the tube, the tube extends and deploys the distal edge of the bladder from a collapsed condition in which it is emplaced within the pericardium to a deployed condition partly encircling the heart. The distal edge of the bladder is of a length such as to extend through an angle of from about 180 degrees to about 270 degrees around the heart proximate to the atrio-ventricular groove with one end located near the pulmonary artery and the other end near the inferior vena cava. Thus, the bladder engages mainly the left ventricle.

In an advantageous arrangement, the non-distensible tube has a finger portion extending distally and adapted to engage the heart between the pulmonary veins. By providing the non-distensible tube with three finger portions extending distally and defining spaces between them, portions of the heart are engaged by the finger portions on opposite sides of the right and left pulmonary veins with the pulmonary veins being received in the spaces. The finger portions, where provided, help retain the bladder in the desired position with the left ventricle.

Further assurance that the bladder will stay in the desired position in engagement with the left ventricle is provided by filling the tube with a particulate material. The particulate material is substantially incompressible, has limited ability to flow, and makes the tube semi-rigid. The tube also fills the space between the epicardium and the pericardium and frictionally engages the outer wall of the epicardium and the inner wall of the pericardium, for further enhancement of the retention.

The bladder has an inner and an outer wall joined to each other along their perimeters. Preferably though not essentially, one of the walls is of a substantially non-extensible material and the other wall is of an extensible material. In such a form, the bladder is extensible primarily in a direction transverse to the surfaces of the parietal pericardium and epicardium and is dimensionally stable circumferentially and axially of the heart. In addition, the non-extensible wall can form one wall of the tube to which the bladder is attached and by which it is deployed.

The apparatus further includes an introducer tube and at least one inserter wire adapted to be passed through the introducer tube. Each inserter wire has a distal end attached to the distal edge of the bladder and having a length such that it is adapted to extend out of the proximal end of the introducer tube for manipulation in order to advance the bladder through the incision in the pericardium and into position between the epicardium and the pericardium. The introducer tube also receives a light conductor, which illuminates of the site of the incision in the pericardium and an image conductor for transmitting an image of the illuminated portion of the pericardium through the introducer tube to its proximal end. The light conductor is connected to a light source, and the image conductor conducts the image of the site of the incision in the pericardium to a CCD camera and its associated electronics for providing input to a television monitor.

According to another aspect of the present invention, a method of providing mechanical assistance to a failing heart comprises, broadly, the following steps: an incision is made in the upper abdomen inferior to the xiphoid process and medial to the border of the left coastal arch, and an introducer tube is inserted through the abdominal incision; the introducer tube is guided to a position medial to the inferior aspect of the heart apex; a portion of the pericardium medial to the inferior aspect of the heart apex is illuminated and an image of the illuminated portion is formed on a monitor; an incision is made in the pericardium to permit the bladder described above to be inserted in collapsed condition; the bladder is guided between the pericardium and the epicardium generally along the posterior aspect of the heart by manipulation of an inserter wire; after the collapsed bladder has reached the desired position, mechanical assistance is provided to the heart by repeatedly pumping a gas under pressure into the bladder and withdrawing the gas from the bladder to compress and release the left ventricle.

The bladder of the present invention functions by compressing the left ventricle when gas under pressure is introduced into the bladder to expand it. The pericardium, which is intact except for a small incision, sustains the reaction load exerted by the inflated bladder, and the acting load of the distended bladder collapses the left ventricle. Because the pericardium has a corset-like relationship to the heart, it sustains the reaction load of the bladder. The bladder need not be made to closely fit to the heart and need not be constructed to support the reaction load of the pumping loads applied to the ventricle. The bladder stays in place between the pericardium and heart, inasmuch as the pericardium remains essentially intact except for the small incision required to allow it to be introduced.

The volumes of the bladder at the ends of heart systole and diastole can be controlled by the gas pump that inflates and deflates the bladder. Accordingly, if the heart is abnormally enlarged (distended), the device enables its size at the end of diastole to be reduced. It is well known that a distended heart pumps less efficiently that a normal sized heart, and the apparatus provides for enhancing the pumping efficiency of a distended heart. Similarly, the volume of the bladder at the end of systole can be established by control of the pump to establish optimal contraction and blood circulation rates.

An important advantage of the device of the present invention is its ability to support blood circulation mechanically without highly invasive surgery, such as open cardiac massage (which requires an emergency thoracotomy) or placement of a mechanical assist device (such as a left ventricular assist device). The only surgical wounds are a relatively small incision in the abdomen and a small incision in the pericardium. The abdominal incision is easily closed; the pericardial incision is left open. The potential for complications in the healing of the wounds is significantly less than more major procedures. The surgery is, of course, vastly easier to perform and can be performed quickly. The assist apparatus can be left in place in the patient for long periods of time, if needed. Removal of the bladder is also simple, inasmuch as it can be pulled out of the pericardium through the small incision through which it was placed. The device does not directly contact the blood. Accordingly, the risk of clotting in the assist apparatus, which is a problem with blood pumps, is totally avoided.

The bladder, the wire or wires for introducing it, the introducer tube and the light and image conductors for the camera can be manufactured as a unit and are disposable. The camera, the monitor, and the pump for operating the bladder can be provided on a cart, which is kept ready for use in a hospital emergency room or operating suite, or installed in a cardiac emergency vehicle.

For a better understanding of the invention, reference may be made to the following description of exemplary embodiments, taken in conjunction with the accompanying drawings.

DESCRIPTION OF THE EMBODIMENTS

Figure 1:
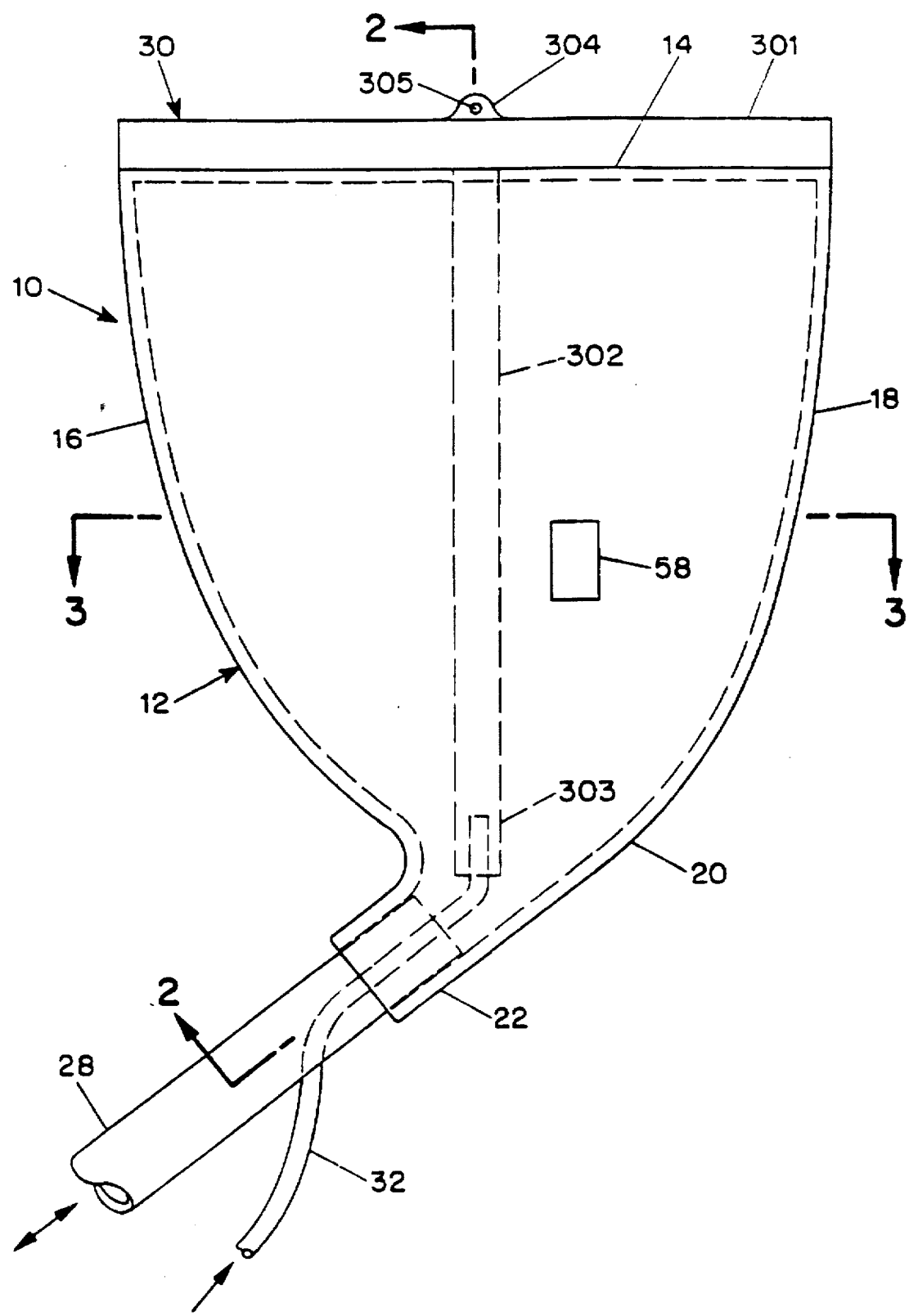
FIG. 1 is a plan view of one embodiment of a bladder.
Figure 2:
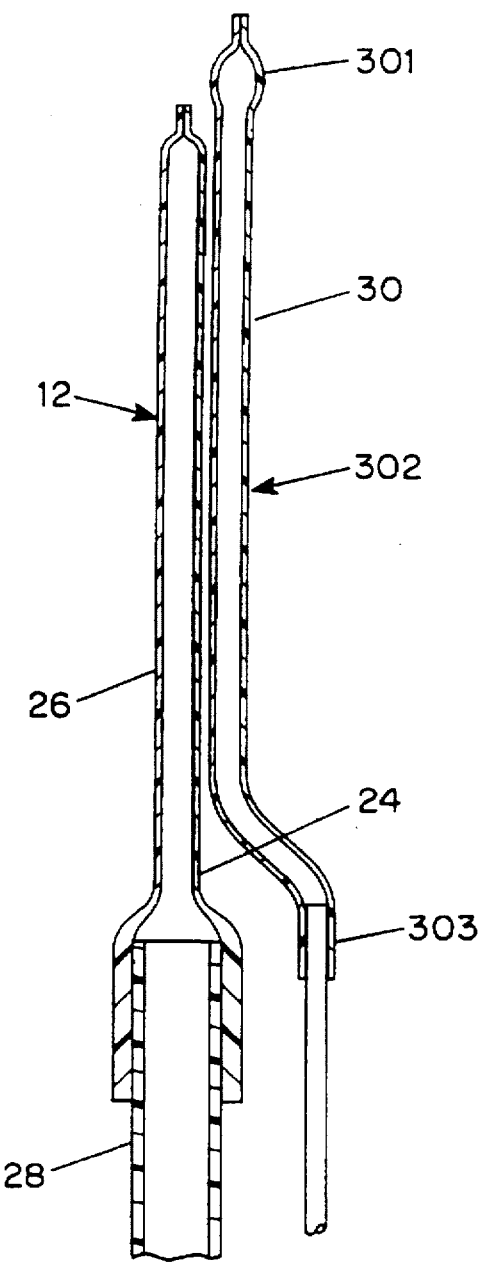
FIG. 2 is a cross-sectional view of the bladder of FIG. 1 taken along a broken plane indicated by the lines 2—2 of FIG. 1.
Figure 3:
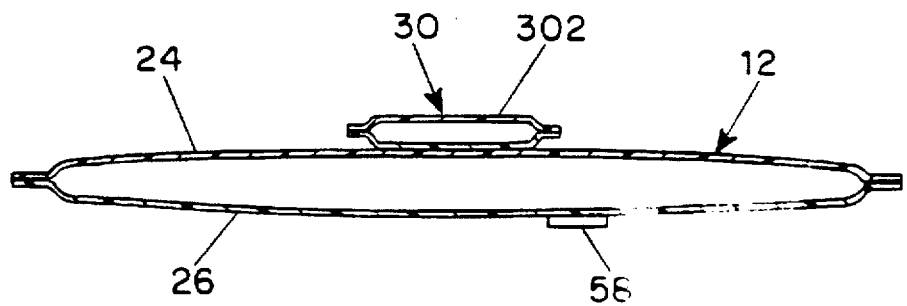
FIG. 3 is a cross-sectional view of the bladder of FIG. 1 taken along lines 3—3 of FIG. 1.

The apparatus 10 shown in FIGS. 1 to 3 includes an inflatable bladder 12 that is made of suitable thin flexible sheet materials that are biologically acceptable for placement in the body. In the flattened condition shown in FIG. 1, the bladder 12 is roughly triangular, having a distal edge 14 that is of a length such that when in place it extends circumferentially around the superior portion of the left ventricle of the heart at a position proximate to the atrioventricular groove through from about 180 degrees to about 270 degrees, one end being located near the pulmonary artery and the other end near the inferior vena cava. The side edges 16 and 18 are curved and are of a length such that when the bladder is in place in engagement with the heart, the proximal apex 20 is located slightly inferiorly of the heart apex. Because the bladder is placed against the heart through an incision at the inferior aspect of the pericardium proximate to the heart apex, the proximal end portion 22 of the bladder leads off somewhat laterally with respect to the vertical axis of the triangle, i.e., in the medial direction anatomically with respect to the heart as viewed from the front.

The bladder is composed of two sheets 24 and 26 of thin, highly flexible sheet material (see FIGS. 2 and 3) joined together along their edges. The sheet 24 is non-extensible, and the sheet 22 is extensible. Accordingly, when inflated, the bladder expands predominantly in a direction perpendicular to the sheets. The sheets are fabricated so that they form conical surfaces that approximately match the shape of the part of the heart that the bladder engages without wrinkling to any great extent. The proximal end portion 22 of the bladder receives and is joined in sealed relation to a length of moderately flexible tubing 28.

The cross-piece portion 301 of a T-shaped tube 30 is attached to the distal edge 14 of the bladder. The leg portion 302 of the tube extends along the triangle axis of the bladder and is preferably attached to the adjacent wall of the bladder along most of its length. The tube is made from T-shaped blanks of a thin, highly flexible non-distensible material joined along their edges. The proximal end 303 of the leg 302 receives and is affixed in sealed relation to a length of moderately flexible tubing 32. A tab 304 having a hole 305 is formed on the edge of the cross-piece portion of the tube 300 and serves as an attachment point for an inserter wire, as described below.

Figure 5:
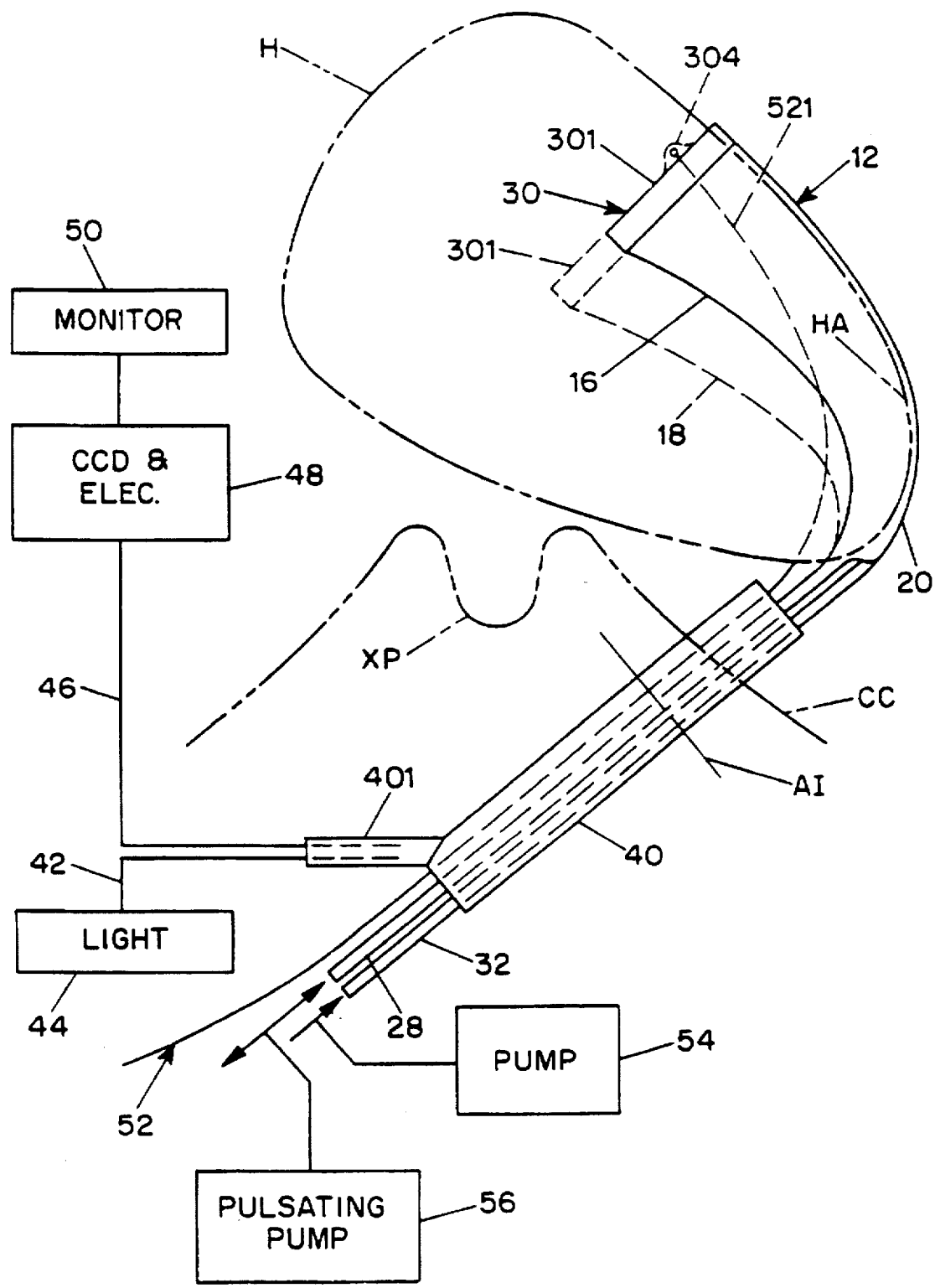
FIG. 5 is a schematic drawing showing other components used in the invention and the use of the invention in a patient.

Referring to FIG. 5, the bladder is placed in engagement with the heart H by minimally invasive surgery. An incision AI about 3 cm long is made in the upper abdomen inferiorly of the xiphoid process XP and medially of the borders of the left coastal arch CA. An introducer tube 40 having a diameter of about 2.5 cm to 3.0 cm is inserted through the abdominal incision AI and is guided to a position proximate to the medial aspect of the heart apex HA. A lateral branch 401 of the tube 40 receives the proximal end portion of a light conductor 42 that leads from a light source 44 and the proximal end portion of an image conductor 46 that leads to a CCD camera and electronics unit 48. The distal end of the light conductor 42 illuminates the path of the introducer as it is being inserted and ultimately illuminates a portion of the pericardium proximate to the medial aspect of the heart apex HA. A lens (not shown) at the distal end of the image conductor 48 receives an image, which is picked up by the camera and is processed to present the image on a monitor 50.

Using a grasping instrument and special scissors that have blades that are presented parallel to the surface of the pericardium, which are inserted through the introducer tube 40, an incision about 2.0 to 2.5 cm long is cut in the medial aspect of the pericardium proximate to the heart apex HA.

The bladder is supplied carefully folded into a collapsed condition, much like a fan, within a placement tube (not shown) and has the distal end 521 of an insertion wire 52 attached to the eye 304 of the bladder. This unit is inserted through the introducer tube 40 and through the incision in the pericardium. The placement tube is removed, and the proximal end of the inserter wire 52 is manipulated to guide the still collapsed bladder along the posterior aspect of the heart both laterally and superiorly. A fluoroscope (not shown) is used to observe the path of the inserter wire 52. Radiological markers may be applied at selected locations to the bladder proximal portion to enable observation of its location fluoroscopically. Manipulation of the part of the tube 28 outside the introducer tube enables the apex of the bladder to be placed slightly inferiorly of the heart apex.

When the bladder has reached the desired position, the tube 32 is attached to a source of gas pressure, such as a hand or manual pump 54 having a reservoir of an inert gas, such as $CO_2$, and gas pressure is applied to the tube 30. The inflation of the tube causes it to extend and push the distal portion of the bladder circumferentially part way around the heart. The tube 28 is connected to a pulsating pump 56 which alternately pumps a gas, such as $CO_2$, into the bladder and suctions the gas back out. The pump may be controlled by ECG signals of the rhythm of the heart if the heart rhythm is regular or by signals from a heart pacer if it is not. To this end, it is advantageous to attach a sensing/pacing electrode 58 to the wall 26 of the bladder that engages the heart. The electrode serves the alternative functions of sensing the heart rhythm when it is regular and of pacing the heart when the rhythm is irregular. The electrode can also be used for defibrillation. For sensing/pacing purposes, the operation of the pump is controlled by signals derived from or delivered to the electrode 58. The pulsating expansion and contraction of the bladder alternately compresses the left ventricle, to deliver blood, and releases it to allow it to fill. The reaction loads of the bladder are borne by the still intact pericardium.

In some patients, it may be beneficial to introduce a second bladder into the pericardium in a position to engage the right ventricle. The second bladder is inflated and deflated in synchronization with the bladder that engages the left ventricle. The tandem operation of the two bladders, which preferably substantially completely surround the ventricular portion of the heart, provides enhanced assistance to the heart muscles, as compared with a single bladder working mainly the left ventricle, and permits better control of both the pulmonary and systemic circulations by proportioning of the pumping displacements of the two bladders.

Figure 4:
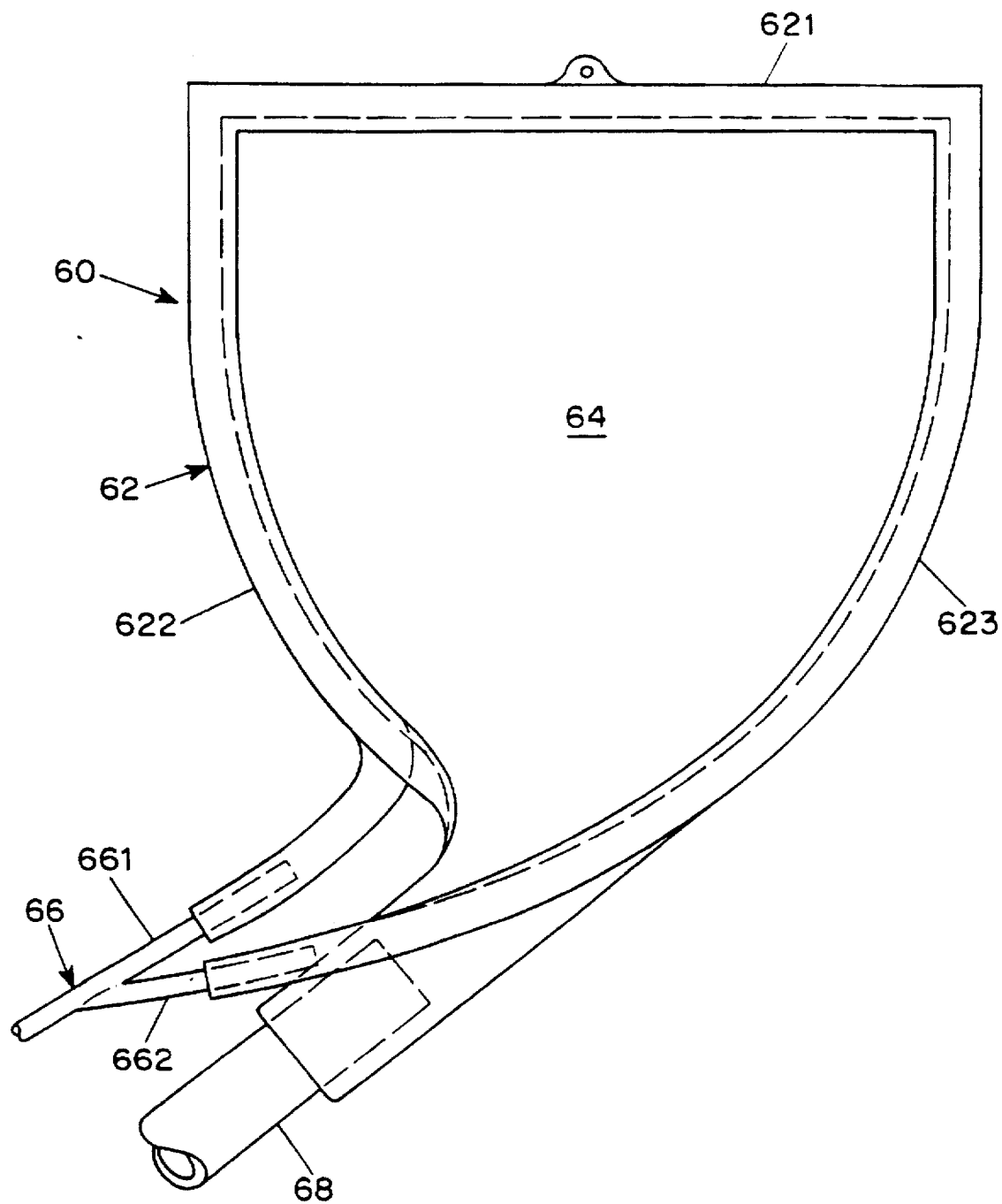
FIG. 4 is a plan view of a second embodiment of a bladder.

The bladder 60 shown in FIG. 4 is essentially the same as the bladder shown in FIGS. 1 to 3, except that it has a non-distensible tube 62 having a distal portion 621 that extends along and is joined to the distal margin of an inflatable bladder 64 and side portions 622 and 623 that extend along and are joined to the respective side margins of the bladder. The ends of the respective side portions 622 and 623 of the non-distensible tube 62 are joined and sealed to branch portions 661 and 662 of a gas supply tube 66, through which a gas under pressure is delivered to inflate the tube 62 and extend the bladder after it has been placed between the pericardium and the heart. A pulsating gas pressure is supplied through a tube 68 joined and sealed to the bladder.

Figure 6:
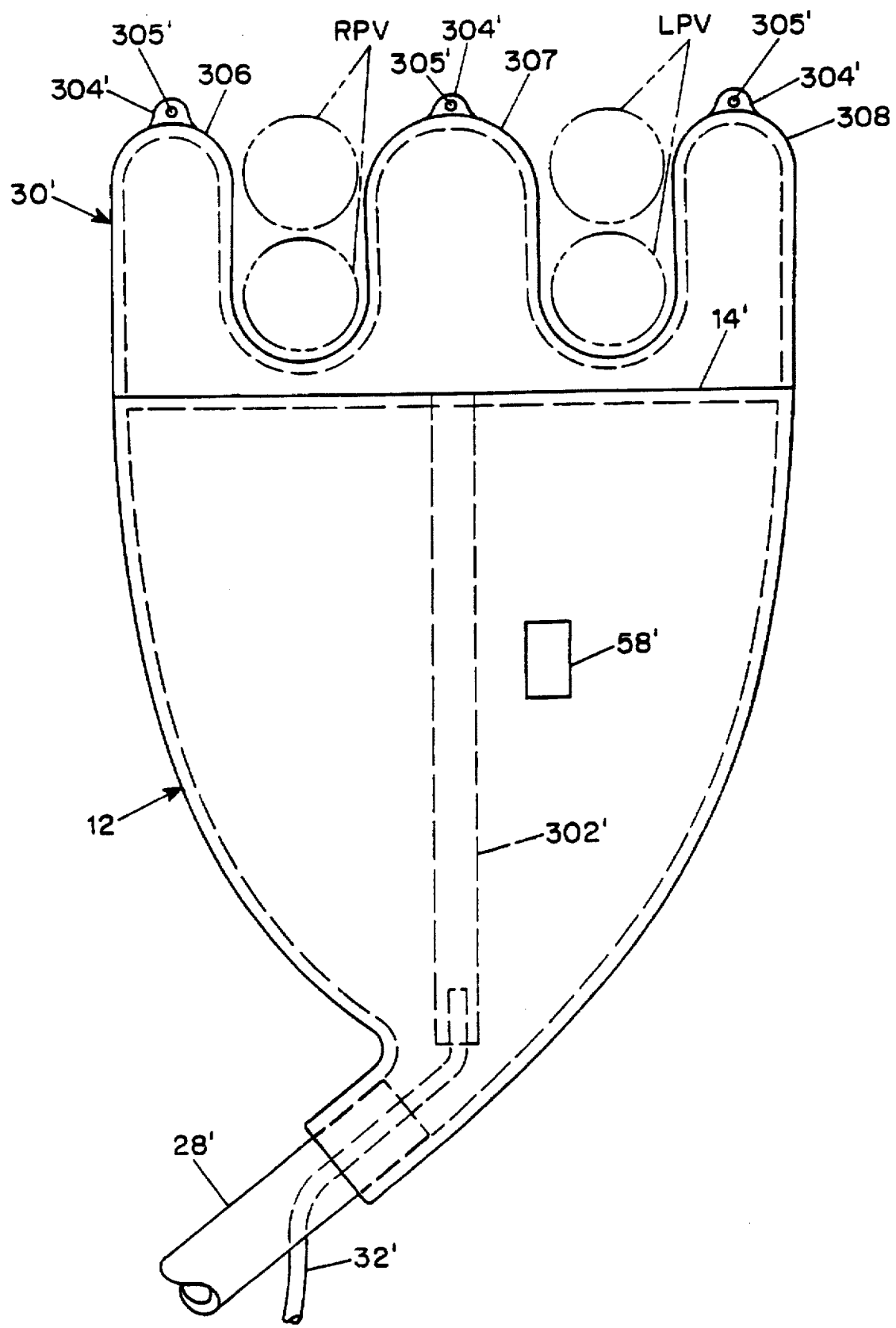
FIG. 6 is a plan view of a third embodiment of a bladder.

The bladder shown in FIG. 6 is similar to the one shown in FIGS. 1 to 3. Accordingly, the same reference numerals are applied, but with a prime suffix to differentiate the embodiment of FIG. 6. The embodiment of FIG. 6 differs from that of FIGS. 1 to 3 in that it has a non-extensible tube 30' having three finger portions 306, 307 and 308 with spaces between them. The finger portions extend distally (with respect to the bladder 12') and are shaped and positioned to engage portions of the heart on opposite sides of the right pulmonary veins RPV and left pulmonary veins LPV, the veins being received in the spaces between the finger portions. Each of the finger portions has on its tip an eyelet 304' with a hole 305' to which an inserter wire can be attached for use in guiding the bladder and tube into the desired position.

Retention of each of the embodiments can be further enhanced, after insertion and extension by supplying air to the tube, by filling the tube with a light-weight particulate material, such as tiny plastic spheres. The particulate material can be introduced through the respective conduit 32, 62, 32' by blowing it in with a gas. The particulate material is essentially non-compressible and has limited fluidity. Accordingly, it fills the space between the epicardium, causes the tube to become semi-rigid, and provides for stable frictional engagement of the tube walls with the outer wall of the epicardium of the heart and the inner wall of the pericardium. In the case of the embodiment of FIG. 6, the stabilizing of the finger portions 306, 307 and 308 by the particulate material is especially beneficial to providing a grip on superior aspects of the heart and better defining the spaces for the pulmonary veins. The particulate material that fills the tube portion 302' extending along the wall of the bladder 12' tends to make that portion behave as a spine, which bridges the bladder in the proximo-distal direction with respect to the tube 28' and increases the stability of the bladder in that direction.

I claim:

1. Cardiac ventricular assist apparatus adapted to be placed between the pericardium and the heart by insertion through an incision in the wall of the upper abdomen below the rib cage and an incision in the inferior aspect of the pericardium proximate to the heart apex comprising a distensible flexible bladder adapted to be passed in a collapsed condition through the incision in the pericardium to a position between the pericardial sac and the epicardium, the bladder being of generally triangular shape and of a size and shape such as to be engageable exclusively with a substantial portion of the outer surface of the left ventricle of a heart, and the bladder having a distal edge of a length such as to extend around the heart proximate to the atrio-ventricular groove through an angle of from about 180 degrees to about 270 degrees from one end near the pulmonary artery to another end near the inferior vena cava, and a tube attached to the bladder through which a gas can be introduced into and withdrawn from the bladder.

2. Apparatus according to claim 1 and further comprising a non-distensible tube joined to the distal edge of the bladder and adapted to be connected to a source of a fluid by which it can be extended after insertion of the bladder to deploy the distal edge of the bladder from a collapsed condition in which it is emplaced within the pericardium to an extended condition partly encircling the heart.

3. Apparatus according to claim 2, wherein the non-distensible tube has a finger portion extending distally and adapted to engage the heart between the pulmonary veins.

4. Apparatus according to claim 2, wherein the non-distensible tube has three finger portions extending distally and defining spaces between them, the finger portions being adapted to engage portions of the heart with the right and left pulmonary veins being received in the spaces.

5. Apparatus according to claim 2, wherein when the bladder and tube are in place in the extended condition in engagement with the heart, the tube is filled with a particulate material.

6. Apparatus according to claim 4, wherein when the bladder and tube are in place in the extended condition in engagement with the heart, the tube is filled with a particulate material.

7. Ventricular assist apparatus according to claim 1 wherein the bladder has an inner and an outer wall joined to each other along their perimeters, one of the walls being of a substantially non-extensible material and the other wall being of an extensible material, whereby the bladder is distensible primarily in a direction perpendicular to the surfaces of the pericardium and epicardium and is dimensionally stable circumferentially and axially to the heart.

8. Ventricular assist apparatus according to claim 7 wherein the bladder walls are fabricated so that they form segments of conical surfaces that approximately match the shape of the part of the heart that the bladder engages without wrinkling.

9. Ventricular assist apparatus according to claim 1 and further comprising an introducer tube and an inserter wire adapted to be passed through the introducer tube and having a distal end attached to the distal edge of the bladder and having a length such that it is adapted to extend out of the proximal end of the introducer tube for manipulation to move the bladder through the incision in the pericardium and into position between the epicardium and the pericardium.

10. Ventricular assist apparatus according to claim 1 and further comprising means received through the introducer tube for conducting light through the introducer tube to illuminate a portion of the pericardium and means received through the introducer tube for transmitting an image of the illuminated portion of the pericardium through the introducer tube to its proximal end.

11. Ventricular assist apparatus according to claim 1 and further comprising a sensing/pacing electrode attached to a wall of the bladder that engages the heart.

12. A method of providing mechanical assistance to a failing heart comprising the steps of making an incision in the upper abdomen inferior to the xiphoid process and medial to the border of the left coastal arch, inserting an introducer tube through the abdominal incision, guiding the introducer tube to a position proximate to the medial aspect of the heart apex, illuminating a portion of the pericardium proximate to the medial aspect of the heart apex and forming on a monitor an image of said portion, making an incision in said portion of the pericardium, providing in collapsed condition an inflatable distensible bladder of generally triangular shape and of a size and shape such as to be engageable exclusively with a substantial portion of the outer surface of the left ventricle of a heart, the bladder having a distal edge of a length such as to extend around the heart proximate to the atrio-ventricular groove through an angle of from about 180 degrees to about 270 degrees from one end near the pulmonary artery to another end near the inferior vena cava, and the bladder being attached to a tube through which a gas can be introduced into it and withdrawn from it, moving the collapsed bladder through the pericardial incision and guiding it along the posterior aspect of the heart by manipulation of an inserter wire, deploying the collapsed bladder to engage it with the left ventricle, and repeatedly pumping a gas under pressure into the bladder and withdrawing the gas from the bladder to compress and release the left ventricle.

13. A method according to claim 12 wherein the bladder has a distal edge that is adapted to be located proximate to the atrio-ventricular groove of the heart and a non-distensible tube joined to the distal edge of the bladder and further comprising the step of connecting the tube to a source of a fluid by which it can be extended after insertion of the bladder to deploy the distal edge of the bladder from a collapsed condition in which it is emplaced within the pericardium to an extended condition partly encircling the heart, and supplying a gas under pressure from the source to the non-distensible tube of the bladder to cause the bladder to extend and envelop at least the left ventricle of the heart.

14. A method according to claim 12 wherein the bladder is moved and guided by attaching at least one inserter wire to the distal edge of the bladder and manipulating a portion of the wire outside of the introducer tube.

15. A method according to claim 12 and further comprising the steps of providing in collapsed condition a second inflatable distensible bladder of a size and shape such as to be engageable with a substantial portion of the outer surface of the right ventricle of the heart and attached to a tube through which a gas can be introduced into it and withdrawn from it, moving the collapsed second bladder through the pericardial incision and guiding it along the anterior aspect of the heart by manipulation of an inserter wire, and repeatedly pumping a gas under pressure into the second bladder and withdrawing the gas from the second bladder in synchronization with the pumping and withdrawing of gas into and from the first bladder to compress and release the right ventricle.

16. A method according to claim 13 and further comprising the step of filling the tube with a particulate material after the bladder and tube are in place in the extended condition in engagement with the heart.

* * * * *